US006284286B1

(12) United States Patent
Arimoto et al.

(10) Patent No.: US 6,284,286 B1
(45) Date of Patent: Sep. 4, 2001

(54) COMPOSITION FOR PREVENTION AND EXTERMINATION OF PLANT DISEASE

(75) Inventors: Yutaka Arimoto, 1-16-15-203, Nobitome, Niiza-shi, Saitama-ken, 352-0011; Isamu Yamaguchi, 1090-1, Negane, Hasuda-shi, Saitama-ken, 349-0131; Yukio Sato, Tokyo; Shigeru Nomura, Takaoka, all of (JP)

(73) Assignees: The Institute of Physical and Chemical Research, Wako; Toagosei Co., Ltd., Tokyo; Yutaka Arimoto, Niiza; Isamu Yamaguchi, Hasuda, all of (JP)

( * ) Notice: Subject to any disclaimer, the term of this patent is extended or adjusted under 35 U.S.C. 154(b) by 0 days.

(21) Appl. No.: 09/115,623

(22) Filed: Jul. 14, 1998

(30) Foreign Application Priority Data

Jul. 15, 1997 (JP) .................................................. 9-190177

(51) Int. Cl.⁷ .................................................. A01N 59/00
(52) U.S. Cl. .......................... 424/682; 424/600; 424/703; 424/709; 424/713; 424/715; 424/717; 424/722; 514/975
(58) Field of Search ............................ 514/975; 424/600, 424/601, 602, 603, 606, 630, 632, 637, 638, 639, 641, 646, 663, 664, 665, 677, 680, 678, 679, 682, 703, 709, 713, 715, 717, 719, 720, 722

(56) References Cited

U.S. PATENT DOCUMENTS 4,228,124 * 10/1980 Kashihara et al. .................... 422/36
4,242,336 * 12/1980 Hasegawa et al. ................ 424/223.8
4,840,959 * 6/1989 Oda et al. ............................ 514/355
5,443,835 * 8/1995 Winston ............................... 424/407
5,547,918 * 8/1996 Newton et al. ...................... 504/116

FOREIGN PATENT DOCUMENTS

| 647 929 | 2/1985 | (CH) . |
| 2 029 701 | 3/1980 | (GB) . |
| 2 213 378 | 8/1989 | (GB) . |
| WO 96/03872 | * 2/1996 | (JP) . |
| WO 96/16539 | * 6/1996 | (JP) . |
| WO 95/08916 | 4/1995 | (WO) . |

OTHER PUBLICATIONS

Derwent Abstracts, AN 88–094608, JP63 044505, Feb. 25, 1998.

Derwent Abstracts, AN 93–096726, JP 05 039206, Feb. 19, 1993.

Derwent Abstracts, AN 92–147523, JP 04 089406, Mar. 23, 1992.

* cited by examiner

*Primary Examiner*—Jose G. Dees
*Assistant Examiner*—Frank Choi
(74) *Attorney, Agent, or Firm*—Oblon, Spivak, McClelland, Maier & Neustadt, P.C.

(57) ABSTRACT

A composition for prevention and extermination of plant disease which comprises a biocidal inorganic compound, an amphoteric surfactant, and at least one member selected from the group consisting of a nonionic surfactant and an anionic surfactant. The composition exhibits residual activity for a long period of time without phytotoxicity.

8 Claims, 1 Drawing Sheet

COMPOSITION FOR PREVENTION AND EXTERMINATION OF PLANT DISEASE

FIELD OF THE INVENTION

This invention relates to a composition for prevention and extermination of plant disease, in particular, a composition which maintains residual activity for a long time and is useful as an agricultural and horticultural biocide. Namely, this invention relates to agricultural chemicals.

PRIOR ART

As compositions for prevention and extermination of plant disease, there have widely been known and sold those comprising, as effective components, biocidal inorganic compounds and those comprising biocidal inorganic compounds and aliphatic polyhydric alcohol ester.

Examples of such agricultural chemicals include an agricultural and horticultural biocide and a composition for prevention and extermination of plant viral disease which comprises sodium hydrogen carbonate and polyglycerin fatty acid ester (JP-B-57-48527) and agricultural chemicals which comprises active ingredient and phospholipid or fatty acid ester of aliphatic polyhydric alcohol (JP-A-1-151501 and JP-A-5-39206).

SUMMARY OF THE INVENTION

An object of the present invention is to improve a composition for prevention and extermination of plant disease comprising biocidal inorganic compound as an active ingredient, and more particularly, to provide a composition for prevention and extermination of plant disease which maintains residual activity for a long time but induces no or little phytotoxicity.

The inventors of the present invention have conducted studies to solve the above object. As a result, they have found that the use of an amphoteric surfactant and at least one of nonionic and/or anionic surfactants in combination with a biocidal inorganic compound prolongs remarkably residual activity of the composition for prevention and extermination of plant disease without increasing phytotoxicity. They have completed the present invention based on this findings.

The present invention provides a composition for prevention and extermination of plant disease which comprises a biocidal inorganic compound, an amphoteric surfactant, and at least one member selected from the group consisting of a nonionic surfactant and an anionic surfactant.

PREFERRED EMBODIMENTS OF THE INVENTION

Figure 1:
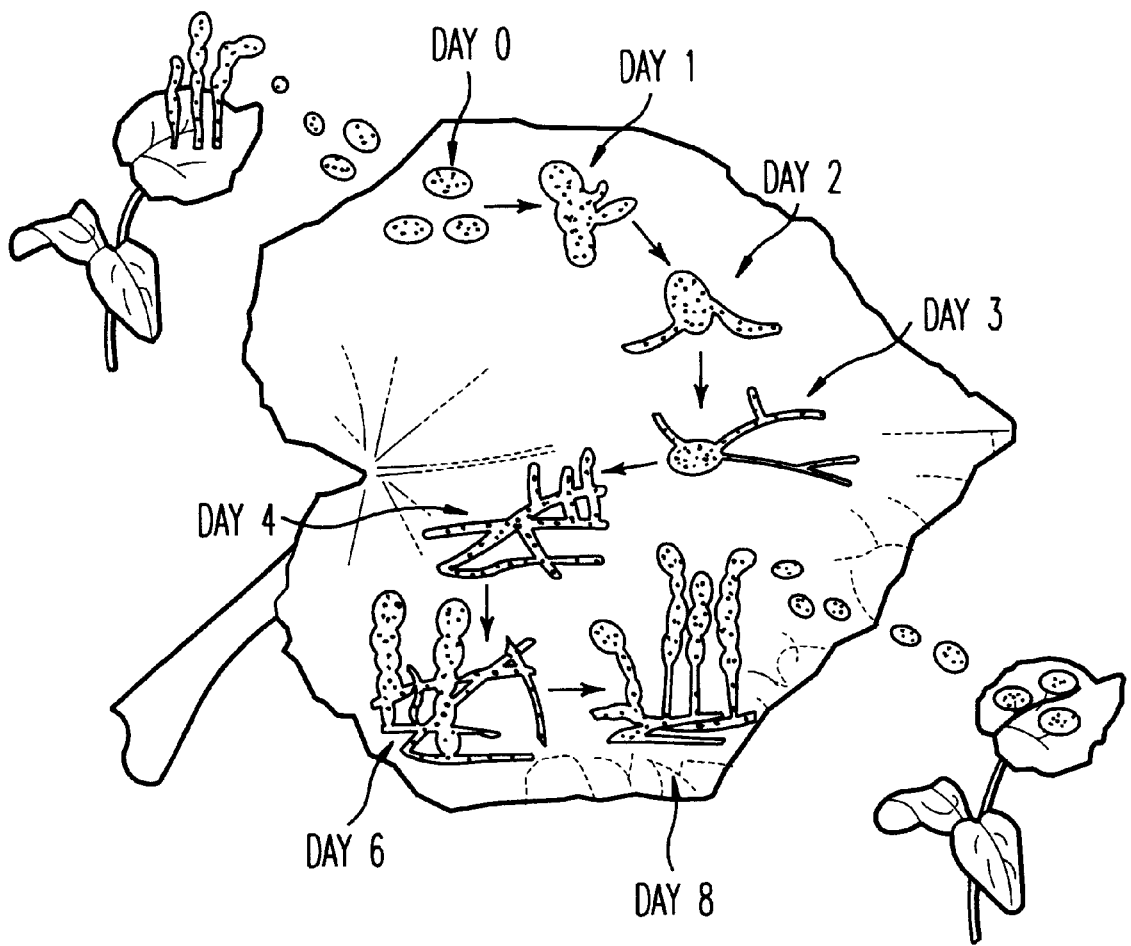
FIG. 1 is a drawing illustrating a relationship between the growing state of cucumber powdery mildew-causing fungi after they are inoculated to leaves of cucumber seedlings and the time lapsed after the inoculation.

The present invention will now be explained in detail.

As biocidal inorganic compounds used in the present invention, there may be mentioned known compounds as described in the prior art statement, such as copper salts such as copper sulfate, basic copper sulfate, cupric chloride, copper chloride, basic copper chloride, cupric hydroxide, basic copper carbonate; and sodium or potassium hydrogen carbonates, carbonates, sulfates, phosphates, pyrophosphates, and chlorides, which are highly stable to plants, such as sodium hydrogen carbonate, potassium hydrogen carbonate, sodium carbonate, potassium carbonate, sodium sulfate, potassium sulfate, sodium phosphate, potassium phosphate, sodium pyrophosphate, potassium pyrophosphate, sodium chloride, potassium chloride; iron sulfate, manganese sulfate, magnesium sulfate, zinc sulfate, aluminum sulfate; ammonium chloride; calcium pyropbosphate; and sulfur which is widely used.

Particularly preferred are sodium salts and potassium salts, such as, carbonates, hydrogen carbonates, phosphates and pyrophosphates; sulfates of copper, iron, manganese, magnesium, zinc and aluminum; and sulfur.

Examples of the amphoteric surfactants used in the present invention include known ones, such as aminocarboxylate such as polyoctyl poly(aminoethyl)glycine, polyalkyl di(aminoethyl)glycine, and N,N-bis(octylaminoethyl) glycine; ether amine oxide such as lauryl dinethyl amine oxide; and carboxy betaine, sulfo betaine, and imidazolinium betaine such as lauryl dinethyl aonium betaine, stearyl dimethyl acetic acid betaine, myristylic acid propanylamide dinethyl acetic acid betaine, alkyl carboxymethyl hydroxyethyl isidazolinium betaine, 2-alkyl-N-hydroxyethyl isidazolinium betaine, and lauryl hydroxy sulfo betaine.

Particularly preferred are aminocarboxylate amphoteric surfactants such as polyoctyl poly(aminoethyl)glycine, polyalkyl di(aminoethyl)glycine, and N,N-bis (octylaninoethyl)glycine; and commercially available products such as OBANOL 516 and OBANOL 512 manufactured by TOHO CHEMICAL INDUSTRIES, Co., Ltd.

Examples of the nonionic surfactants used in the present invention include alkylol aside, polyoxyethylene alkylphenyl ether, polyoxyethylene alkyl ether, polyethyleneglycol fatty acid ester, sorbitan fatty acid ester, polyoxyethylene sorbitan fatty acid ester, and polyoxyethylene polyoxypropylene alkyl ether, more specifically, lauric acid diethanol amide, polyoxyethylene nonylphenyl ether, polyoxyethylene lauryl ether, sonooleic acid polyethylene glycol, sorbitan distearate, and polyoxyethylene polyoxypropylene alkyl ether. Particularly preferred are polyoxyethylene alkyl ether, among which polyoxyethylene $C_8$–$C_{18}$ alkyl ether wherein the solar number of added ethylene oxide is 3 to 15, preferably 6 to 8 and the carbon number of the alkyl group is 6 to 18, preferably 10 to 14, for example, polyoxyethylene lauryl ether.

Examples of the anionic surfactants used in the present invention include sulfosuccinate, phosphoric acid ester, alkylsulfate, and polyoxyethylene alkyl ether sulfate, particularly dioctyl sodium sulfosuccinate.

In the composition of the present invention, conventional additives for agricultural chemicals may be used similarly. For example, an appropriate filler can be used depending on the oil absorption required for the composition. Examples of such fillers include powdery inorganic compounds, such as white carbon, talc and diatomaceous earth. As a fire retardant for formulations containing sulfur, such compounds as magnesium sulfate and aluminum oxide say be used. There say also be used powdery products of nature such as sugars, for example, gum Arabic, lactose and sorbitol.

In the composition of the present invention, the amount of the amphoteric surfactant is preferably 1 to 40 parts by weight, more preferably 3 to 25 parts by weight and most preferably 5 to 10 parts by weight per 100 parts by weight of the biocidal inorganic compound, and the amount of at least one member selected from the group consisting of a nonionic surfactant and an anionic surfactant is preferably 1 to 40 parts by weight, more preferably 2 to 25 parts by weight and most preferably 5 to 10 parts by weight per 100 parts by weight of the biocidal inorganic compound. If the amount of the amphoteric surfactant is less than one part by weight or the amount of the nonionic surfactant and/or the anionic surfactant is less than one part by weight, the effect of the present invention is not always sufficiently obtained, while if they exceed 40 parts by weight, the concentration of the active ingredient decreases relatively and the effect of the present invention is not always sufficiently obtained.

Fillers may be used in an amount conventionally used, for example, 5 to 30 parts by weight per 100 parts by weight of the biocidal inorganic compound.

If the active ingredient (i.e., the biocidal inorganic compound) is inflammable substance such as sulfur, a fire retardant may be used in an amount depending on the required degree of fire retardance, for example, 50 to 100 parts by weight per 100 parts by weight of the biocidal inorganic compound.

The composition of the present invention may be prepared according to the method disclosed in JP-A-1-151501, namely, using appropriate dispersing medium (such as water and organic solvent), or it may also be prepared by simple mixing by the use of a mixer of high mixing efficiency without the use of dispersing medium (such as water and organic solvent).

The composition of the present invention my be diluted with water to 1/50 to 1/2000 and applied to various plants.

The amounts of the components in the diluted composition liquid are preferably 2.0 to 0.05% by weight of the bio cidal inorganic compound, 0.1 to 0.005% by weight of the amphoteric surfactant, 0.1 to 0.001% by weight of the nonionic surfactant and 0.1 to 0.005% by weight of the anionic surfactant.

EXAMPLES

The composition of the present invention will now be explained more specifically with reference to formulation examples, test examples and comparative examples, to which the present invention is not limited.

Formulation Example 1

Powdery potassium hydrogen carbonate (100 mesh pass) (400 g), dioctyl di(aminoethyl)glycine (50 g) and dioctyl sodium sulfosuccinate (25 g) were kneaded, and white carbon (25 g) was added followed by sufficient kneading to prepare a white powdery composition for prevention and extermination of plant disease.

Formulation Example 2

Powdery potassium hydrogen carbonate (100 mesh pass) (400 g), dioctyl di(aminoethyl)glycine (50 g), polyoxyethylene lauryl ether (the molar number of added ethylene oxide =8)(25 g) and white carbon (25 g) were mixed followed by sufficient kneading to prepare a white powdery composition for prevention and extermination of plant disease.

Formulation Example 3

To powdery sodium hydrogen carbonate (100 mesh pass) (400 g), a mixture of dioctyl di(aminoethyl)glycine (50 g) and polyoxyethylene sodium sulfosuccinate (the molar number of added ethylene oxide =3)(25 g) was added and kneaded, and white carbon (25 g) was added to prepare a white powdery composition for prevention and extermination of plant disease.

Formulation Example 4

To powdery potassium carbonate (200 mesh pass)(350 g), a mixture of lauryl hydroxy sulfo betaine (50 g) and polyoxyethylene lauryl ether (the molar number of added ethylene oxide =7)(50 g) was added and kneaded, and white carbon (25 g) was added to prepare a white powdery composition for prevention and extermination of plant disease.

Formulation Example 5

To powdery sodium hydrogen carbonate (100 mesh pass) (350 g), lauryl dimethyl amine oxide (50 g) and dioctyl sodium sulfosuccinate (50 g) were added, and white carbon (50 g) was added to prepare a white powdery composition for prevention and extermination of plant disease.

Formulation Example 6

To powdery sulfur (100 mesh pass)(250 g), dioctyl di(aminoethyl)glycine (50 g) and polyoxyethylene oleyl ether (the molar number of added ethylene oxide=8)(50 g) were added and kneaded, and magnesium sulfate (150 g) was added to prepare a yellow powdery composition for prevention and extermination of plant disease.

Formulation Example 7

To powdery sulfur (100 mesh pass)(400 g), dioctyl di(aminoethyl)glycine (25 g) and dioctyl sodium sulfosuccinate (25 g) were added, and white carbon (25 g) was added and kneaded to prepare a yellow powdery composition for prevention and extermination of plant disease.

Formulation Example 8

To water (100 g), powdery sulfur (100 mesh pass)(350 g), dioctyl di(aminoethyl)glycine (25 g) and polyoxyethylene lauryl ether (the molar number of added ethylene oxide =8)(25 g) were added and agitated to prepare a yellow dispersion of a composition for prevention and extermination of plant disease.

Formulation Example 9

To water (100 g), powdery sulfur (100 mesh pass)(350 g), dioctyl di(aminoethyl)glycine (25 g) and dioctyl sodium sulfosuccinate (25 g) were added and agitated to prepare a yellow dispersion of a composition for prevention and extermination of plant disease.

Comparative Formulation Example 1

Glycerin monooleate (2 g) was dissolved in acetone (100 cc), to which powdery sodium hydrogen carbonate (100 mesh pass)(80 g) was added and agitated sufficiently. Then, the solvent was fully removed by distillation using a rotary evaporator to prepare a powder. Casein soda powder (10 g) was added to the powder and nixed to prepare a wettable powder having good mobility.

Comparative Formulation Example 2

Polyglycerin fatty acid ester (1 g) was dissolved in acetone (100 cc), to which powdery sodium hydrogen carbonate (100 mesh pass)(80 g) was added and agitated sufficiently. Then, the solvent was fully removed by distillation using a rotary evaporator to prepare a wettable powder.

Comparative Formulation Example 3

Glycerin monooleate (0.5 g) and glycerin monooctoate (0.3 g) were dissolved in acetone (100 cc), to which powdery sodium carbonate (100 mesh pass)(80 g) was added and agitated sufficiently. Then, the solvent was fully removed by distillation using a rotary evaporator to prepare a powder. Casein soda powder (10 g) was added to the powder and mixed to prepare a wettable powder having good mobility.

Comparative Formulation Example 4

To powdery sodium chloride (60 mesh pass)(400 g), white carbon (100 g) was added and agitated sufficiently for 30 minutes, to which diglycerin oleate (40 g) heated to 60° C. was added and agitated for 30 minutes. Then, lauryl dihydroxyethyl amine (60 g) was added and agitated for 30 minutes to prepare a white powdery composition.

Comparative Formulation Example 5

To powdery potassium sulfate (100 mesh pass)(300 g), powdery sulfur (600 mesh pass)(250 g) and powdery talc (300 g) were added and agitated sufficiently for 30 minutes, to which a mixture of glycerin monolaurate (50 g) and polyoxyethylene alkylallyl ether (100 g) melt at 70° C. were added and agitated for 30 minutes to prepare a yellow powdery composition for prevention and extermination of plant disease.

Comparative Formulation Example 6

To powdery potassium sulfate (100 mesh pass)(50 g), powdery sulfur (600 mesh pass)(375 g) and white carbon (25 g) were added and agitated sufficiently for 30 minutes, to which glycerin monooleate (50 g) was added and agitated for 30 minutes to prepare a yellow powdery composition for prevention and extermination of plant disease.

Evaluation Test 1

The compositions for prevention and extermination of plant disease prepared In Formulation Examples 1 to 5 and Comparative Formulation Examples 1 to 4 were subjected to the following evaluation test. The compositions were evaluated according to preventive values before and after development of the disease.

Method for Evaluation of Preventive Value Before and After Development of the Disease Conidia of powdery mildew-causing fungi were inoculated to the first true leaves of cucumber (100 to 150 conidia per leaf) and cultured in a glass greenhouse at 20 to 30° C. and 40 to 80% RH. After about 7 days and disease spots were formed, the composition for prevention and extermination of plant disease diluted 800 times with water was sprayed on the leaves in an amount of 4 ml per leaf. The diluted composition was also sprayed on the second true leaves on which disease spots had not yet been observed.

The plants were maintained in the glass greenhouse after the spray. After 14 days, the number of disease spots developed on the second true leaves were counted and compared with that of control (untreated division) to obtain a preventive value before the development of lesion according to the following equation 1.

Equation 1:

$$\text{A preventive value before the development of lesion } (\%) = (1 - A/B) \times 100$$

wherein A is the number of disease spots developed on the second true leaves after 14 days of the spray of the composition, and B is the number of disease spots developed on the second true leaves after 14 days in untreated division.

Further, after 10 and 14 days, the number of healed disease spots (C) and that of recovered disease spots (D) on the first true leaves were counted. A curative value was obtained according to the following equation 2.

Equation 2:

$$\text{A curative value after the development of lesion } (\%) = C/(C+D) \times 100$$

wherein C is the number of healed disease spots on the first true leaves after 10 or 14 days of the spray of the composition, and D is the number of recovered disease spots on the first true leaves after 10 or 14 days of the spray of the composition.

Test Example 10 is a control wherein water was sprayed. Results are shown in Table 1.

After 4 to 5 days of infection of seedlings of cucumber with powdery mildew, conidia are formed in the form of chain on the tip of conidiophore and make mounds in white color which make it possible to observe disease spots with naked eyes. If the diluted composition is sprayed, the conidia are washed away and the mounds are collapsed and flattened. However, disease spots are still observable with naked eyes.

If the sprayed composition is not sufficient in effect, conidia are formed again to make mounds of disease spots with time after the application of the composition. A disease spot on which a mound is observed wholly or at least partially is judged to be a disease spot wherein pathogenic fungi survive. Such a disease spot is called herein "recovered disease spot". In contrast, if the sprayed composition is sufficient in effect to totally kill the powdery mildew-causing fungi, conidia are no longer formed and mounds of disease spots remain collapsed and flattened. A disease spot which remains collapsed and flattened after 2 weeks of the application of the composition is judged to be a disease spot wherein pathogenic fungi are totally killed. Such a disease spot is called herein "healed disease spot".

TABLE 1

Test Results of Evaluation of Compositions

| Test No. | Composition No. | Appearance | Preventive value 10 days | Curative Value 10 days | Curative Value 14 days | Phyto-toxicity |
|---|---|---|---|---|---|---|
| 1 | Ex. 1 | Homogeneous | 93 | 100 | 100 | no |
| 2 | Ex. 2 | Homogeneous | 98 | 100 | 100 | no |
| 3 | Ex. 3 | Homogeneous | 95 | 100 | 100 | no |
| 4 | Ex. 4 | Homogeneous | 97 | 100 | 95 | no |
| 5 | Ex. 5 | Homogeneous | 96 | 100 | 96 | no |
| 6 | Comp. Ex. 1 | Homogeneous | 0 | 65 | 18 | no |
| 7 | Comp. Ex. 1 | Homogeneous | 22 | 90 | 28 | no |
| 8 | Comp. Ex. 1 | Homogeneous | 8 | 92 | 32 | no |
| 9 | Comp. Ex. 1 | Homogeneous | 0 | 28 | 8 | yes |
| 10 | Water | Homogeneous | 0 | 0 | 0 | no |

All the wettable powder solutions were homogeneous and cloudy in white.

Evaluation Test 2

The compositions for prevention and extermination of plant disease prepared in Formulation Examples 6 to 9 and Comparative Formulation Examples 5 and 6 were subjected to the same evaluation test as the test 1 except that the dilution was changed as shown in Table 2 and the amount sprayed was 2 ml per leaf. Preventive and curative values were obtained according to the equations 1 and 2 for the disease spots after 21 days and 14 days, respectively.

Test Example 17 is sulfur flovable commercially available and Test Example 18 was a control wherein water was sprayed. Results are shown in Table 2.

TABLE 2

Test Results of Evaluation of Compositions

| Test No. | Composition No. | Concentration | Appearance | Curative value 14 days | Preventive value 21 days |
|---|---|---|---|---|---|
| 11 | Ex. 6 | × 2000 | Homogeneous | 100 | 100 |
| 12 | Ex. 7 | × 4000 | Homogeneous | 100 | 100 |
| 13 | Ex. 8 | × 3000 | Homogeneous | 100 | 100 |
| 14 | Ex. 9 | × 3000 | Homogenecus | 100 | 100 |
| 15 | Comp. Ex. 5 | × 2000 | Homcgeneous | 82 | 65 |
| 16 | Comp. Ex. 6 | × 4000 | Homogeneous | 73 | 38 |
| 17 | Sulfur Flowable | × 500 | Homogeneous | 45 | 85 |
| 18 | Water | | Clear | 0 | 0 |

Evaluation Test 3 (Test for Curative Effects)
Growing Process of Cucumber Powdery Mildew-Causing Fungi and Effects of the Composition In the similar manner to the procedures in the evaluation test 1, cucumber seedlings were inoculated with cucumber powdery mildew-causing fungi and then immediately divided 11 groups. To each of the groups, the composition of Formulation Example 2 or Comparative Formulation Example 1 diluted 800 times with water was sprayed on the leaves in an amount of 4 al per leaf. Group I was sprayed on the day of the inoculation (after 0 day of the inoculation), Group 2 after one day of the inoculation, Group 3 after two days of the inoculation, and in the same way, Group 10 after nine days of the inoculation and Group 11 was not treated.

The cucumber seedlings were grown in the glass greenhouse. After two weeks of the inoculation, the number of disease spots developed were counted and a preventive value was obtained according to the following equation 3. Equation 3.

A preventive value $(\%) = (1 - E/F) \times 100$ wherein E is the number of disease spots in the treated division, and F is that in untreated division. Results are shown in Table 3.

TABLE 3

| Days after inoculation | Preventive value (%) Ex. 2 | Preventive value (%) Comp. Ex. 1 |
|---|---|---|
| 0 | 100 | 100 |
| 1 | 100 | 64 |
| 2 | 100 | 25 |
| 3 | 100 | 5 |
| 4 | 100 | 8 |
| 5 | 100 | 18 |
| 6 | 100 | 31 |
| 7 | 100 | 68 |
| 8 | 95 | 95 |
| 9 | 98 | 100 |

Concentration: 100 mg/800 ml
Amount sprayed: 5 ml/seedling

Cucumber seedlings as shown in the separate sheet were used in the experiments.

FIG. 1 is a schematic drawing illustrating the growth of cucumber powdery mildew-causing fungi after inoculation. After one day of the inoculation, conidia of the cucumber powdery mildew-causing fungi sprout and extend germ tubes. After two days, hypha is further extended and after three days, hypha branches off. After four days, conidiophore is formed. After six days, conidia are formed and after eight days, conidia fly vigorously.

The composition of Comparative Example 1 showed high preventive effect when sprayed immediately after the inoculation, but the preventive values decreased to 64% after one day of the inoculation, 25% after two days and very low level after 3 to 5 days. However, the preventive values increased after around 6 days of the inoculation when the formation of conidia begins and reached to 95% after 8 days of the inoculation.

In contrast, the composition of Example 2 showed high prevention effects always in the growing process from just after the inoculation to 8 days of the inoculation when the conidia begin to fly.

The above results teach that the composition of Comparative Example 1 has high prevention effect against the conidia of the cucumber powdery mildew-causing fungi but low prevention effects against the hypha, while the composition of Example 2 has high prevention effects against not only the conidia of the cucumber powdery mildew-causing fungi but also the hypha.

Duration of the effects of both the compositions will now be discussed.

Usually, there exist powdery mildew-causing fungi at various growing stages on cucumber leaves as illustrated in FIG. 1. The composition of Comparative Example 1 has high preventive effect against conidia and therefore the disease spots already formed (wherein conidia are formed vigorously) will disappear. Only the stage at which the conidia are formed can be observed with naked eyes. Even if the disease spots disappear, the hypha are still alive and conidia are formed again in 4 to 5 days to make disease spots again observable with naked eyes.

Since the action of the composition against hypha is weak, the composition does not inhibit the growth of powdery mildew-causing fungi at the growing stage at which conidia were not formed at the application of the composition. Thus, the fungi can form disease spots which say be observed with naked eyes after 4 to 5 days at the earliest.

Namely, in the composition of Comparative Example 1, new disease spots may be formed or recovery may be observed after 4 to 5 days of the application. This means that the preventive effect of the composition of Comparative Example 1 lasts 4 to 5 days.

In contrast, the composition of Example 2 has high preventive effect against not only conidia but also hypha. Accordingly, if the composition of Example 2 is applied to cucumber leaves in the state as illustrated in FIG. 1, all the powdery mildew-causing fungi on the leaves are killed. Further, since the composition is also effective after 5 days of the application against conidia which come from outside by flying, the fungi cannot grow on the leaves. Accordingly, if the composition of Example 2 is applied, new disease spots will not be developed before 12 to 14 days of the application. Duration of the preventive effects of the composition of Example 2 is remarkably longer than that of the prior art compositions.

Evaluation Test 4

The same test as in Evaluation Test 3 was conducted except that compositions having components as shown in Table 4 were used.

| KHCO$_3$: Potassium hydrogen carbonate | 80 mg |
| MG: Glycerin monocaprylate | 5 mg |
| Amine: Lauryl hydroxyl amine | 5 mg |
| Amphoteric surfactant A: dioctyl diaminoethyl glycine | 10 mg |
| Surfactant B: polyoxyethylene nonylphenyl ether | 5 mg |
| Surfactant C: polyoxyethylene alkyl ether | 5 mg |
| Surfactant D: dioctyl sodium sulfosuccinate | 5 mg |
| Sizing agent: carboxymethylcellulose | 5 mg |

At least one of the above components dissolved in 100 ml of distilled water was applied in an amount of 5 ml per one pot. After 3 days, 5 days, 7 days, 10 days and 12 days of the application, preventive effects were evaluated. Results are shown in Table 4.

TABLE 4

| | Components | | | | | | | | Preventive effects (%) | | | | |
| --- | --- | --- | --- | --- | --- | --- | --- | --- | --- | --- | --- | --- | --- |
| Ex. | KHCO3 | MG | Amine | Size | A | B | C | D | 3 | 5 | 7 | 10 | 12 |
| 1 | 80 | — | — | — | — | — | — | — | 25 | 0 | 0 | 0 | 0 |
| 2 | — | — | 5 | — | — | — | — | — | 0 | 0 | 0 | 0 | 0 |
| 3 | — | — | — | 5 | — | — | — | — | 0 | 0 | 0 | 0 | 0 |
| 4 | — | — | — | — | 10 | — | — | — | 0 | 0 | 0 | 0 | 0 |
| 5 | — | — | — | — | — | 5 | — | — | 0 | 0 | 0 | 0 | 0 |
| 6 | — | — | — | — | — | — | 5 | — | 0 | 0 | 0 | 0 | 0 |
| 7 | — | — | — | — | — | — | — | 5 | 0 | 0 | 0 | 0 | 0 |
| 8 | 80 | 5 | — | — | — | — | — | — | 53 | 12 | 0 | 0 | 0 |
| 9 | 80 | — | 8 | — | — | — | — | — | 48 | 15 | 0 | 0 | 0 |
| 10 | 80 | — | — | 9 | — | — | — | — | 21 | 0 | 0 | 0 | 0 |
| 11 | 80 | — | — | — | — | 5 | — | — | 22 | 0 | 0 | 0 | 0 |
| 12 | 80 | — | — | — | — | — | 5 | — | 45 | 0 | 0 | 0 | 0 |
| 13 | — | — | — | — | — | — | — | 5 | 33 | 0 | 0 | 0 | 0 |
| 14 | 80 | 5 | 5 | — | — | — | — | — | 53 | 25 | 0 | 0 | 0 |
| 15 | 80 | 5 | 5 | — | — | 5 | — | — | 68 | 48 | 0 | 0 | 0 |
| 16 | 80 | 5 | 5 | 5 | — | — | 5 | — | 68 | 56 | 16 | 0 | 0 |
| 17 | 80 | 5 | 5 | — | — | — | — | 5 | 57 | 33 | 0 | 0 | 0 |
| 18 | — | 5 | 5 | — | — | — | — | — | 34 | 0 | 0 | 0 | 0 |
| 19 | — | 5 | 5 | — | — | 5 | — | — | 41 | 10 | 0 | 0 | 0 |
| 20 | — | — | 5 | — | — | 5 | — | — | 8 | 0 | 0 | 0 | 0 |
| 21 | — | — | 5 | — | — | — | 5 | — | 5 | 0 | 0 | 0 | 0 |
| 22 | 80 | — | — | — | 10 | — | — | — | 43 | 35 | 24 | 10 | 0 |
| 23 | 80 | — | — | — | 10 | 5 | — | — | 100 | 100 | 100 | 98 | 95 |
| 24 | 80 | — | — | — | 10 | — | 5 | — | 100 | 100 | 100 | 100 | 98 |
| 25 | 80 | — | — | — | 10 | — | — | 5 | 100 | 100 | 100 | 97 | 90 |
| 26 | — | — | — | — | 10 | — | 5 | — | 25 | 18 | 6 | 0 | 0 |

In Table 4, Examples 23 to 25 are those of the present invention. It is clear that only the compositions of Examples 23 to 25 which comprise all of a biocidal inorganic compound, an amphoteric surfactant, and at least one member selected from the group consisting of a nonionic surfactant and an anionic surfactant exhibit high preventive effects for a long period of time.

Evaluation Test 5 (Test for Preventive Effects)

The compositions of Formulation Example 2 and Comparative Formulation Example 1 were used for the test for preventive effects.

Cucumber seedlings (at 0.5 to 0.9 leaf stage before the inoculation of powdery mildew-causing fungi) were divided into 7 groups. To each of the groups, the composition diluted 800 times with water was sprayed on the leaves in an amount of 4 ml per leaf. Group 1 was sprayed on the first day, Group 2 on the second day, Group 3 on the third day, and in the same way, Group 7 on the seventh day. After Group 7 was sprayed and the sprayed liquid was dried, powdery mildew-causing fungi (100 to 150 conidia per leaf) were inoculated to the cucumber seedlings (including those to which the composition was sprayed on the first to seventh day and untreated one). The seedlings were grown in the glass greenhouse at 20 to 30° C. and 40 to 50% RH. After 14 days of the inoculation, the number of disease spots formed on the first leaves was counted to obtain a preventive value according to the following equation.

Equation:

A preventive value (%)=(1−[the number of disease spots in the treated seedlings]/the number of disease spots in the untreated seedlings])×100

Results are shown in Table 5.

TABLE 5

| Group | | 1 | 2 | 3 | 4 | 5 | 6 | 7 |
|---|---|---|---|---|---|---|---|---|
| Days after spray and until inoculation | | 6 | 5 | 4 | 3 | 2 | 1 | 0 |
| Composition | Dilution | Preventive value (%) | | | | | | |
| Ex. 2 | × 800 | 70 | 85 | 98 | 100 | 100 | 100 | 100 |
| Comp. Ex. 1 | × 800 | 0 | 0 | 0 | 0 | 0 | 20 | 60 |

Table 5 shows that the composition of the present invention exhibits a preventive value of 100% if the fungi is inoculated 3 days after the composition is sprayed (see Groups 4 to 7), and a preventive value of 70% if the fungi is inoculated 6 days after the composition is sprayed (see Group 1). In contrast, the composition of Comparative Example 1 exhibits a preventive value of only 60% if the fungi is inoculated immediately after the composition is sprayed (see Group 7), and a preventive value of only 20% if the fungi is inoculated one day after the composition is sprayed (see Group 6) and does not exhibit any preventive effect if the fungi is inoculated more than one days after the composition is sprayed (see Groups 5 to 1).

Evaluation Test 6 (Test for Preventive Effects)

The compositions of Formulation Example 6 and Comparative Formulation Example 5 were used for the test for preventive effects.

Cucumber seedlings (at 0.5 to 0.9 leaf stage before the inoculation of powdery mildew-causing fungi) were divided into 4 groups. To each of the groups, the composition diluted 2000 times (Formulation Example 6) or 600 times (Comparative Formulation Example 5) with water was sprayed on the leaves in an amount of 2 ml per leaf. Powdery mildew-causing fungi (100 to 150 conidia per leaf) were inoculated to the cucumber seedlings (including those to which the composition was sprayed on the first and untreated one) of Group 1 after 7 days of the spraying, of Group 2 after 14 days of the spraying, of Group 3 after 21 days of the spraying and of Group 4 after 28 days of the spraying. The seedlings were grown in the glass greenhouse at 20 to 30° C. and 40 to 80% RH. After 14 days of the inoculation, the number of disease spots formed on the first leaves was counted to obtain a preventive value in the similar manner to Evaluation Test 5. Results are shown in Table 6.

TABLE 6

| Group | | 1 | 2 | 3 | 4 |
|---|---|---|---|---|---|
| Days after spray and until inoculation | | 7 | 14 | 21 | 28 |
| Composition | Dilution | Preventive value (%) | | | |
| Ex. 6 | × 2000 | 100 | 100 | 96 | 81 |
| Comp. Ex. 5 | × 600 | 100 | 98 | 53 | 26 |

Table 6 shows that the composition of the present invention exhibits a preventive value of 100% if the fungi is inoculated 7 days or 14 days after the composition diluted 2000 times is sprayed (see Groups 1 and 2), and a preventive value of 96% or 81% if the fungi is inoculated 21 days or 28 days after the composition is sprayed (see Groups 3 and 4). In contrast, the composition of Comparative Example 5 exhibits a preventive value of 100% if the fungi is inoculated 7 days after the composition diluted 600 times is sprayed (see Group 1), but a preventive value is reduced to 98%, 53% or 26% if the fungi is inoculated 14 days, 21 days or 28 days after the composition is sprayed (see Groups 2 to 4).

The composition of the present invention for prevention and extermination of plant disease exhibits sufficient curative and preventive effects for a long period of time without phytotoxicity against plant diseases such as cucumber powdery mildew, tomato powdery mildew, strawberry powdery mildew, wheat powdery mildew, onion rust disease, coffee rust disease, cucumber gray sold, and tomato gray sold.

What is claimed is:

1. A composition for treatment of plant disease which comprises a biocidal inorganic compound selected from the group consisting of potassium hydrogen carbonate, sodium hydrogen carbonate, potassium carbonate, sulfur and magnesium sulfate, an amphoteric surfactant, and at least one member selected from the group consisting of a nonionic surfactant and an anionic surfactant, wherein said amphoteric surfactant is at least one member selected from the group consisting of polyoctyl poly(aminoethyl)glycine, polyalkyl di(aminoethyl)glycine, N,N-bis(octylaminoethyl) glycine; lauryl dimethyl amine oxide; lauryl dimethyl ammonium betaine, stearyl dimethyl acetic acid betaine, myristylic acid propanylamide dimethyl acetic acid betaine, alkyl carboxymethyl hydroxyethyl imidazolinium betaine, 2-alkyl-N-hydroxyethyl imidazolinium betaine, and lauryl hydroxy sulfo betaine; said nonionic surfactant is a polyoxyethylene $C_8$–$C_{18}$ alkyl ether, and said anionic surfactant is a polyoxyethylene alkyl ether sulfate.

2. The composition for treatment of plant disease of claim 1, wherein the amphoteric surfactant is at least one member selected from the group consisting of polyoctyl poly (aminoothyl)glycine, polyalkyl di(aminoethyl)glycine, and N,N-bis(octylaminoethyl )glycine.

3. The composition for treatment of plant disease of claim 1, wherein the nonionic surfactant is at least one member selected from the group consisting of alkylol aside, polyoxyethylene alkylphenyl ether, polyoxyethylene alkyl ether, polyethyleneglycol fatty acid ester, sorbitan fatty acid ester, polyoxyethylene sorbitan fatty acid ester, and polyoxyethylene polyoxypropylene alkyl ether.

4. The composition for treatment of plant disease of claim 1, wherein the polyoxyethylene $C_8$–$C_{18}$ alkyl ether is polyoxyethylene $C_8$–$C_{18}$ alkyl ether wherein the solar number of added ethylene oxide is 3 to 15.

5. The composition for treatment of plant disease of claim 4, wherein the polyoxyethylene $C_8$–$C_{18}$ alkyl ether wherein the solar number of added ethylene oxide is 3 to 15 is polyoxyethylene lauryl ether wherein the molar number of added ethylene oxide is 5 to 9.

6. The composition of claim 1, wherein the amphoteric surfactant is present in an amount of 1 to 40 parts by weight per 100 parts by weight of said biocidal inorganic compound and the nonionic or anionic surfactant is present in an amount of 1 to 40 parts by weight per 100 parts by weight of said biocidal inorganic compound.

7. A composition for treatment of plant disease which comprises a biocidal inorganic compound selected from the group consisting of potassium hydrogen carbonate, sodium hydrogen carbonate, sulfur, magnesium sulfate and potassium carbonate, an amphoteric surfactant selected from the group consisting of polyoctyl poly(aminoethyl)glycine, polyalkyl di(aminoethyl)glycine and N,N-bis(octylaminoethyl)glycine, and at least one member selected from the group consisting of a nonionic surfactant and an anionic surfactant wherein the nonionic surfactant is selected from the group consisting of polyoxyethylene alkylphenyl ether, polyoxyethylene alkyl ether, polyethyleneglycol fatty acid ester, polyoxyethylene sorbitan fatty acid ester and polyoxyethylene-polyoxypropylene alkyl ether, and the anionic surfactant is a sulfosuccinate, wherein the amphoteric surfactant is present in an amount of 1 to 40 parts by weight per 100 parts by weight of said biocidal inorganic compound and the anionic or nonionic surfactant is present in an amount of 1 to 40 parts by weight per 100 parts by weight of said biocidal inorganic compound.

8. The composition for treatment of plant disease of claim 7, wherein the anionic surfactant is dioctyl sodium sulfosuccinate.

\* \* \* \* \*